United States Patent
Fisk

(10) Patent No.: US 9,161,556 B2
(45) Date of Patent: Oct. 20, 2015

(54) CONTINUOUS CELLULOSTIC PRE-TREATMENT AND BIO-MASS PROCESSING BY REACTIVE EXTRUSION

(76) Inventor: Donald L. Fisk, Rolla, MO (US)

(*) Notice: Subject to any disclaimer, the term of this patent is extended or adjusted under 35 U.S.C. 154(b) by 815 days.

(21) Appl. No.: 13/365,325

(22) Filed: Feb. 3, 2012

(65) Prior Publication Data

US 2012/0125324 A1    May 24, 2012

Related U.S. Application Data

(63) Continuation-in-part of application No. PCT/US2010/044649, filed on Aug. 6, 2010.

(60) Provisional application No. 61/258,669, filed on Nov. 6, 2009, provisional application No. 61/232,278, filed on Aug. 7, 2009.

(51) Int. Cl.
| | |
|---|---|
| A23L 1/00 | (2006.01) |
| C08H 8/00 | (2010.01) |
| C10L 1/00 | (2006.01) |
| C12P 7/10 | (2006.01) |
| D21B 1/16 | (2006.01) |
| C10L 1/02 | (2006.01) |
| C11B 1/00 | (2006.01) |

(52) U.S. Cl.
CPC ............... *A23L 1/0076* (2013.01); *C08H 8/00* (2013.01); *C10L 1/023* (2013.01); *C11B 1/00* (2013.01); *C12P 7/10* (2013.01); *D21B 1/16* (2013.01); *C10G 2300/1014* (2013.01); *C12P 2201/00* (2013.01); *Y02E 50/16* (2013.01)

(58) Field of Classification Search
CPC ........... A23L 1/0076; C08H 8/00; C10L 1/23; C12P 7/10; C12P 2201/00; D21B 1/16; C10G 2300/1014; Y02E 50/16
USPC .................... 127/1, 37; 536/56, 124; 100/117
See application file for complete search history.

(56) References Cited

U.S. PATENT DOCUMENTS

| | | |
|---|---|---|
| 4,901,635 A | 2/1990 | Williams |
| 5,705,369 A | 1/1998 | Torget et al. |

FOREIGN PATENT DOCUMENTS

WO    WO 2011017587 A1 *   2/2011

OTHER PUBLICATIONS

The Written Opinion for PCT International Application No. PCT/US2010/044649, which published as International Publication No. WO 2011/017587 A1, dated Sep. 20, 2010.*

*Primary Examiner* — David A Reifsnyder
(74) *Attorney, Agent, or Firm* — Lucas & Mercanti, LLP

(57) ABSTRACT

Cellulosic materials are treated with Supercritical Carbon Dioxide in an extruder. Machine configuration and operating parameters are strictly controlled in a manner to enhance the ability of Supercritical $CO_2$ to enter into the cells. This results in a controlled deterioration of the cell walls, increasing the reactivity of cellulose and also enhancing the rate and the extent of cellulose hydrolysis. This precisely controlled combination of pressure, shear & temperature accelerates the penetration of carbon dioxide molecules into the crystalline structures, thus more glucose is produced from cellulosic materials after the cell is destructurized as compared to those without the pretreatment increasing glucose yield by as much as 50%. Concurrent saccharification and fermentation tests also show the increase in the available carbon source from the cellulosic materials for fermentation to produce ethanol. As the system operates at low temperature, it will not cause degradation of sugars such as those treated with the high-temperatures involved in many systems discussed.

9 Claims, 4 Drawing Sheets

CONTINUOUS CELLULOSTIC PRE-TREATMENT AND BIO-MASS PROCESSING BY REACTIVE EXTRUSION

CROSS-REFERENCE TO RELATED APPLICATION

This application is a Continuation-in-part of PCT/US2010/044649 filed Aug. 6, 2010 which claimed the priority of U.S. Provisional Patent Application Ser. Nos. 61/232,278, filed Aug. 7, 2009, and 61/258,669 filed Nov. 6, 2009, the contents of all three Applications are incorporated herein by reference.

FIELD OF THE INVENTION

The present invention relates to methods where cellulosic materials are treated with Supercritical Carbon Dioxide in an extruder. In particular, the invention relates to machine configuration and operating parameters that are strictly controlled in a manner to enhance the ability of Supercritical $CO_2$ to enter into the cells. This results in a controlled deterioration of the cell walls, increasing the reactivity of cellulose and also enhancing the rate and the extent of cellulose hydrolysis.

BACKGROUND OF THE INVENTION

Bio-fuels provide a viable route to aid in providing critical transportation energy needs in the US. They can also help in addressing global political instability evolving from reliance on foreign fuel. At present, most bio-fuels produced as ethanol are generated from corn starch. But this can meet only a small portion of US fuel requirements. Plant cellulose is an acceptable source of bio-energy, and its conversion for cellulosic bio-energy crops, which are both abundant and renewable, is a promising alternative approach.

Cost of effectively breaking down cellulose into fermentable sugars has been a major issue slowing cellulosic ethanol production. Many methods have been developed over the years to aid in the conversion of cellulose fibers into fermentable sugars. However, even with today's technology, conversion of lignocellulosic biomass of these crops into fermentable sugars for bio-fuels requires relatively expensive pretreatment processes that can also result in unwanted residuals that may interfere with the fermentation process.

A few of the methods applied in the pretreatment process include Dilute Acid, Flowthrough, Partial Flow, Controlled pH, AFEX, ARP, Supercritical $CO_2$ Explosion, and Lime. In addition, these processes are either expensive, time consuming or both. Currently, pretreating cellulose with acid is a common way to break the material down into fermentable sugars. Most of these systems result in unwanted by-products from the process. The general perception is that these by-product compounds are detrimental and should be removed. Thus, after acid pretreatment, the resulting material is washed and detoxified. That can remove nutrients necessary for efficient fermentation. Washing, detoxifying and adding nutrients back into the pretreated cellulose are three separate steps with each step being expensive, adding to the already high cost of processing bio-fuel.

Claims for minimizing losses from by-product residuals have been made by proponents of the Ammonia Fiber Expansion (AFEX) explosion system with research indicating that chemical compounds that are created when the cellulose fibers go through the ammonia fiber process can improve the overall fermentation process. Developers claim that with this process the cellulose doesn't have to be washed or detoxified, allowing ethanol to be created from cellulose without added nutrients or other steps. Developers are working to improve the efficiency of the system in an attempt to lower its cost.

SUMMARY OF THE INVENTION

A novel approach is a method described as applying ultrasonic energy to a biomass. To process and obtain alcohol, it employs ultrasonic energy as the only means of pretreatment. In the biomass conversion to alcohol using ultrasonic energy, the cellulose material is placed in a reactor under pressurized carbon dioxide at 35° C. for a controlled time period. Upon an explosive release of the carbon dioxide pressure, the destructurization of the cellulosic structure increases the accessible surface area of the cellulosic substrate to enzymatic hydrolysis. The power and frequency of the ultrasonic energy are sufficient to produce cavitational forces in the processing stream at an intensity and duration which causes at least a portion of the lignin to be loosened or removed from the cellulose. This allow an increased amount of cellulose to be hydrolyzed into one or more individual component sugars, wherein conversion of the one or more individual component sugars into one or more fermented individual component sugars during fermentation is increased. Thereafter distilling and dehydrating the one or more fermented individual component sugars produce ethanol and residuals, wherein ethanol yield is increased by applying the ultrasonic energy as claimed.

In another method, cellulosic materials that were treated with Supercritical Carbon Dioxide to increase the reactivity of cellulose to enhance the rate and the extent of cellulose hydrolysis have been tried. The Supercritical Carbon Dioxide would be effective for pretreatment of cellulose as the $CO_2$ would penetrate the cell walls under pressure, thus, facilitating faster destructurization of the cellulose cells. Research using conventional pressurized holding systems that followed by rapid release, to achieve an "explosion" have been met with limited success.

The subject discovery overcomes the obstacles to the earlier methods of fiber expansion, greatly increasing productivity while reducing the cost of pretreatment processes that utilize these "explosion" or "expansion" approaches. This is accomplished by utilizing an extruder to implement continuous flow of the cellulose fibers through a pretreatment process. It has been discovered that the operating conditions based on the same principals utilized in expanding modified prime starch to achieve rapid expansion, achieves the desired "pretreatment" effect of de-structurization of cellulose fibers. These specialized operating parameters include a select combination of: screw element configuration, flow design, temperature control, rotation speed, shear and pressure at the exit from the extruder that provides for instantaneous decompression, achieves a thorough pretreatment of the individual fibers. Recapture and continuous reprocessing of volatiles back through the system results in considerable chemical cost, savings as well as a safer operating environment. The system produces no toxic or hazardous emissions, making the process a benign, environmentally friendly manufacturing procedure, and generating a positive impact.

Results indicate that Supercritical Carbon Dioxide is an effective for pretreatment of cellulose. The controlled shear of the cell walls along with strict control of the pressure facilitates the faster penetration of carbon dioxide molecules into the crystalline structures, thus more glucose is produced from cellulosic materials after the expansion as compared to those without the pretreatment. This expansion pretreatment enhances the rate of cellulosic material hydrolysis as well as increases glucose yield by as much as 50%. Results from the simultaneous saccharification and fermentation tests also show the increase in the available carbon source from the cellulosic materials for fermentation to produce ethanol. As an alternative method, this Supercritical Carbon Dioxide explosion has a possibility to reduce expense compared with ammonia explosion, and since it is operated at the low temperature, it will not cause degradation of sugars such as those treated with steam explosion due to the high-temperature involved.

BRIEF DESCRIPTION OF DRAWINGS

The present invention will be further understood and appreciated by reading the following description in conjunction with the accompanying drawings, in which.

DETAILED DESCRIPTION OF THE INVENTION

Figure 1:
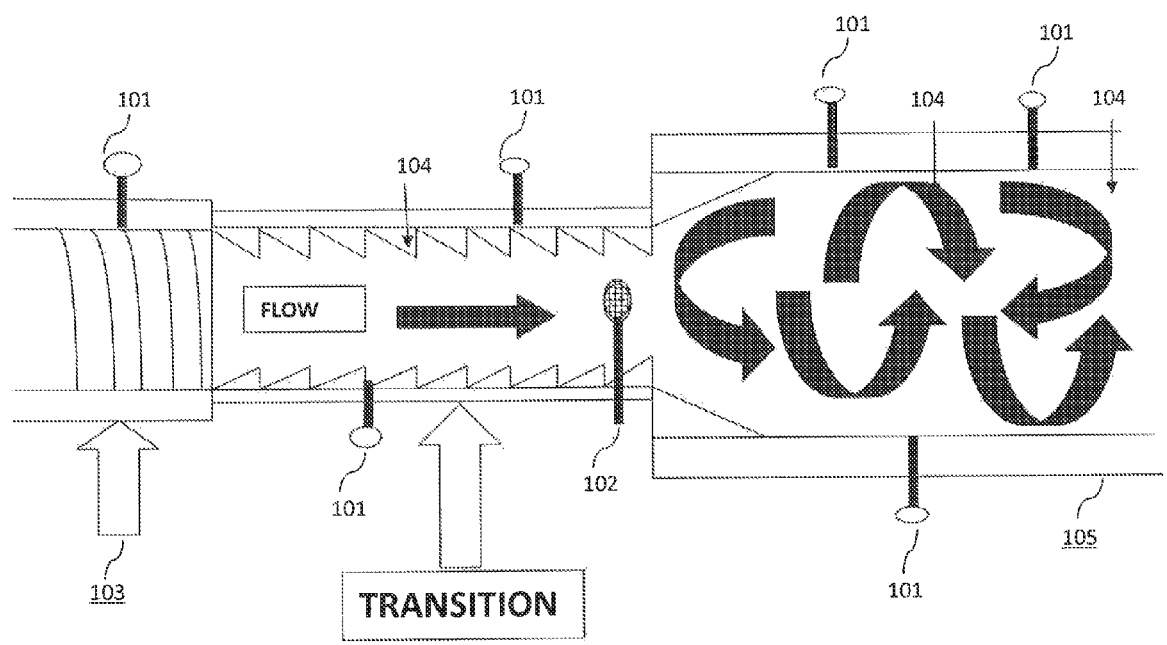
FIG. 1 illustrates the continuous flow processing utilizing pressurized or Supercritical Fluids (CFP)

In the method being described here, cellulosic materials are treated with Supercritical Carbon Dioxide in an extruder. Machine configuration and operating parameters are strictly controlled in a manner to enhance the ability of Supercritical $CO_2$ to enter into the ceils. This results in a controlled deterioration of the cell walls, increasing the reactivity of cellulose and also enhancing the rate and the extent of cellulose hydrolysis. This precisely controlled combination of pressure, shear & temperature accelerates the penetration of carbon dioxide molecules into the crystalline structures, thus more glucose is produced from cellulosic materials after the cell disruption as compared to those without the pretreatment increasing glucose yield by as much as 50%. Concurrent saccharification and fermentation tests also show the increase in the available carbon source from the cellulosic materials for fermentation to produce ethanol. As the system operates at low temperature, it will not cause degradation of sugars such as those treated with the high-temperatures involved in many systems discussed.

Results indicate that Supercritical Carbon Dioxide is effective for pretreatment of cellulose. The controlled shear of the cell walls along with strict control of the pressure facilitates the faster penetration of carbon dioxide molecules into the crystalline structures, thus more glucose is produced from cellulosic materials after the expansion as compared to those without the pretreatment. This expansion pretreatment enhances the rate of cellulosic material hydrolysis as well as increases glucose yield by as much as 50%. Results from the simultaneous saccharification and fermentation tests also show the increase in the available carbon source from the cellulosic materials for fermentation to produce ethanol. As an alternative method, this Supercritical Carbon Dioxide explosion has a possibility to reduce expense compared with ammonia explosion, and since it is operated at the low temperature, it will not cause degradation of sugars such as those treated with steam explosion due to the high-temperature involved.

A second option utilizing the supercritical fluid system is pretreating the grain bran by-product created by the dry milling process. Bio-fuels are an important economic factor in addressing the transportation energy needs in the US. They can also help in addressing global political instability evolving from reliance on foreign fuel. At present, most bio-fuels produced as ethanol are generated from corn starch. The corn kernel has three principal components: the pericarp, the endosperm, and the germ. The tip cap is the component that attaches the kernel to the cob. The germ is a small portion of the kernel that can be recognized on one surface. The germ has oil, protein and enzymes that start the germination process for growth. The outer fibrous layer is the pericarp, or bran, which protects the kernel. The majority of the kernel is endosperm. The endosperm contains approximately 98 percent of the starch in the kernel and is approximately 83 percent of the dry weight of the kernel.

There are approximately 50 patents that address processes to break the kernel into its components; there are approximately another dozen or so patents in application, or patent pending. The challenge has been to determine methods which will generate value-added revenue streams from the process by-products, providing economical solutions to the existing, inefficient fuel ethanol plants as well as for the new plants corning on line in the future by maximizing the utilization of the total feed stock. The benefits of our new method of optimizing the by-product processing will be obvious to the reader.

For the ethanol process, starch is the constituent of the corn that is converted to alcohol. The conventional starch to ethanol process included mashing and fermentation of the corn which is mechanically simple, but from a chemical and biological standpoint the process is quite complex. Fermentation is completed in 40-60 hours. The fats and fiber in the fermenter remain untouched and concentrate as the starch is converted to ethanol. The beer is then sent to the distillation area to strip away the ethanol. The water and ail solids (protein, fat and fiber) are collected from the distillation base and referred to as whole stillage. This whole stillage is then centrifuged to separate the coarse solids from the liquid. The liquid is referred to as thin stillage, which is recycled to the beginning of the process or concentrated in the evaporator to become Corn Condensed Distillers Solubles. The coarse solids collected from the centrifuge are called wetcake. Wetcake and condensed solubles are then combined and dried in a rotary dryer to form the feed coproduct Distillers Dried Grains with Solubles. However much of the protein is lost in the process.

In the method being described here, the aforementioned non-starch components can be sourced from either method of ethanol production. They are transported through a series of actions in a process system designed to achieve predetermined results while being subjected to specified elements or chemicals while they are subjected to shear & pressure in an extruder. Machine operating parameters and configuration are strictly controlled to exert specific energy into the material enhancing the ability of selected Fluids to enter into and partially solubilize the cells. This precisely controlled combination of pressure, shear & temperature accelerates the penetration the molecules/cells allowing these selected Fluids into the amorphous structures partially disrupting the solids resulting in a controlled deterioration of the cell walls. Pressure increases as the material moves to the exit port and discharged into the second stage treatment section where a predetermined pressure and temperature is maintained by infusion of Supercritical Fluid into the material as it is being intimately mixed. This precisely controlled combination of pressure, shear & temperature accelerates the penetration by the selected reactant, including Supercritical Fluids if appropriate, into the cellulose ceils allowing these selected Fluids into the amorphous structures during the time frame the feedstock is held under pressure in Supercritical state. The feedstock is instantly depressurized upon release from the static mixer resulting in a violent expansion causing destructurization of the cells.

The ability of selected Supercritical Fluids to act as reactive solvents enhances the rate and the degree of oil and protein separation. Cellulose pretreatment is also achieved increasing hydrolysis capability, thus more glucose is produced from the grain through utilization of the cellulosic portion due to the cell destructurization as compared to bran without the pretreatment increasing glucose yield of the cellulosic portion by as much as 50%. As the system operates at low temperature, it will not cause degradation of the component parts of the DG's.

The subject discovery overcomes many obstacles known to inhibit secondary process of corn ethanol by-product processing, greatly increasing productivity and profitability. Recapture and continuous reprocessing of volatiles back through the system results in considerable chemical cost savings as well as a safer operating environment. The system produces no toxic or hazardous emissions, making the process a benign, environmentally friendly manufacturing procedure, generating a positive impact throughout the plant area. When utilized with the fractionation system, this process obtains higher quality corn germ proteins and increased yields of corn oil resulting in higher valued co-products. However, the system can also accommodate the use of DGS generated from whole kernel ethanol processes making it a very flexible, process application.

In the processes described in this disclosure, the subject material can be any natural cellulosic bearing material such as corn stalks, corn fiber, switchgrass, woody plants, etc, as long as the material is reduced in a particle size so as to allow entrance into the extruder or pump at maximum through-put capacity. This aids in the maintenance of desired pressure throughout the extrusion system. Of particular interest is the cellulostic fiber by-product resulting from the corn based ethanol production procedure that normally is included in the Distillers Grain by-product including but not limited to Bran, Distillers Grains with Solubles & Distillers Dried Grains with Solubles. However, any numbers of possible feed stocks are useful to the process of the invention For example, FIG. 1 shows the Conceptual drawing of Continuous Flow Processing Utilizing Pressurized or Supercritical Fluids (CFP) With Emphasis on Gas Backflow Inhibitor (Transition). The process can utilize any source of cellulosic fiber such grains, grasses, woody plants, etc. Two basic methods can be utilized.

In one method, the feed stock is sized prior to introduction into the process system by any number of mechanical systems but preferred Is a pin mill whereby the cellulose fibers are substantially reduced in size and partially ruptured from mechanical energy. The sized feed stock is then forced into a transition designed to resist gas backflow via an extruder or a high pressure solids pump into the static mixer where supercritical carbon dioxide is injected under a minimum of 1400 PSI into the feed stock at a ratio range of 10% to 90% of the volume of the feed stock. Feed stock temperature is to be maintained at no less than 90° F. throughout the process.

In another method, the feed stock source has already reduced the size, such as corn fiber, sawdust, bran from a grain dehulling system, etc. These materials can be fed directly into an extruder designed to generate sufficient energy to partially rupture the feed stock as it is being transported thru the extruder and forced into the transition, designed to resist gas backflow, into the static mixer where a pressurized or supercritical fluid, preferably $CO_2$, is injected under a minimum of 1400 PSI into the feed stock at a ratio determined by the fluid used, but no less than 10% of the volume of the feed stock, 90° F. is the minimum feed stock temperature throughout the process.

For purposes of the invention, the term "bran" includes ail of the grain nutrients produced in processes intended to remove or utilize the starch portion regardless of the source or method of reduction, including fractionation, decortication, wet and dry milling processes including but not limited to, those described herein.

For purposes of the invention, the term "Distillers Grains with Solubles" (DGS) is a term generally used to refer to the co-products of the grain fermentation industry. DGS generally have relatively high moisture content (above 50%). Most of the DGS is dried to about 10 to 15% moisture as the shelf life of the wet DGS is 2 to 3 days but some is available as a liquid feed ingredient. The quality and composition of DGS can be affected by a number of factors including the original substrate, the process used, and evaporation procedures.

For purposes of the invention, the term "Distillers Dried Grains with Solubles" (DDGS) are recovered in the distillery and contain all the nutrients from the incoming corn less the starch. Thus the DDGS has at least three fold as much nutrients as the incoming grain. Approximately 4% of the amino acid in corn is broken down and then reconverted to the more nutritionally valuable microbial types. Since the stillage is recycled, the ratio of these more valuable amino acid types continues to increase so that eventually they represent approximately 16% of the final DDGS's amino acid content. No other feed ingredient, (corn gluten teed or meal, soybean meal, etc) results from such a great percentage of microbial products and their back, stocking. The yeast also provides increased vitamins, particularly the B-complex group. DDGS typically analyzes as 27% protein, 11% fat and 9% fiber.

For purposes of the invention, the term "Protein" is the total protein content of the corn germ from both wet-, and dry-milling processes is usually between 14 and 16 wt % but there is significant loss of proteins in the current wet milling process. Proteins in commercial dry-milled corn germ are similar to those found in the corn germ embryo but significantly different from proteins in wet-milled corn germ. In addition the amount of acid precipitated protein was significantly less in wet-compared to dry-milled corn germ. Proteins in commercial dry-milled corn germ are similar to those found in the corn germ embryo. The amount of protein is significantly less in wet-compared to dry-milled corn germ.

For purposes of the present invention, the term "Vegetable Oil" is most of the oil in a Corn, Maize or Grain Sorghum is concentrated in one portion of the kernel called the "germ" (or embryo).

For purposes of this Application, the term Destructurize means the act of altering the structure of cellulosic biomass which is necessary to make the cellulose more accessible to enzymes that convert the carbohydrate polymers into fermentable sugars.

For purposes of this Application, the term Supercritical $CO_2$ means a state of carbon dioxide where it is held at or above its critical temperature and critical pressure. (Minimally; 1100 psi and 88 degrees F.) at which point it is neither a liquid nor a gas.

For purposes of this Application, the term Preconditioned Feedstock means feedstock that has been processed, preferably by mechanical means, to obtain a targeted particle size and moisture content.

The preceding described discoveries are intended to provide added efficiencies and lower the cost of the processes by which the non-starch portions of a starch to ethanol process are converted higher value added by-products.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present subject matter. For example, cellulose fiber disruption is also useful for biomass-based production facilities which produce alcohols other than ethanol. Such alcohols include, but are not limited to, food grade alcohol, industrial alcohols such as methanol, isopropanol, butanol, and so forth, further including propane diol, which can be used to make bioplastics. It is also likely that cellulose fiber disruption would be useful in biomass-based production facilities that produce various organic acids, such as Succinic or Malic acid. Most likely such production facilities which produce alcohols other than ethanol and/or organic acids consist of processes which utilize pretreatment technologies and processes described herein. Therefore, it is manifestly intended that embodiments of this invention be limited only by the claims and the equivalents thereof.

Turning now to the Figures, each of the Figures will be described.

FIG. 1 illustrates the continuous flow processing utilizing pressurized or Supercritical Fluids (CFP) with emphasis on gas backflow inhibitor, displaying Pressure/Temperature Transducers (101), Supercritical Fluid Injection Point (102), Single or Twin Screw Extruder or HP Pump (103), Gas Seals (104), and Static Mixer (105).

Conceptual drawing of Continuous Flow Processing Utilizing Pressurized or Supercritical Fluids (CFP) With Emphasis on Gas Backflow Inhibitor (Transition) is shown in FIG. 1. The process can utilize any source of cellulosic fiber such grains, grasses, woody plants, etc. Two basic methods can be utilized as discussed below.

In the first basic method, the feed stock is sized prior to introduction into the process system by any number of mechanical systems but preferred is a pin mill whereby the cellulose fibers are substantially reduced in size and partially ruptured from mechanical energy. The sized feed stock is then forced into a transition designed to resist gas backflow via an extruder or a high pressure solids pump into the static mixer where supercritical carbon dioxide is injected under a minimum of 1400 PSI into the feed stock at a ratio range of 10% to 90% of the volume of the feed stock. Feed stock temperature is to be maintained at no less than 90° F. throughout the process.

In the second basic method, the feed stock source has already reduced the size, such as corn fiber, sawdust, bran from a grain dehulling system, etc. These materials can be fed directly into an extruder designed to generate sufficient energy to partially rupture the feed stock as it is being transported thru the extruder and forced into the transition, designed to resist gas backflow, into the static mixer where a pressurized or supercritical fluid, preferably $CO_2$, is injected under a minimum of 1400 PSI into the feed stock at a ratio determined by the fluid used, but no less than 10% of the volume of the feed stock. 90° F. is the minimum feed stock temperature throughout the process.

Figure 2:
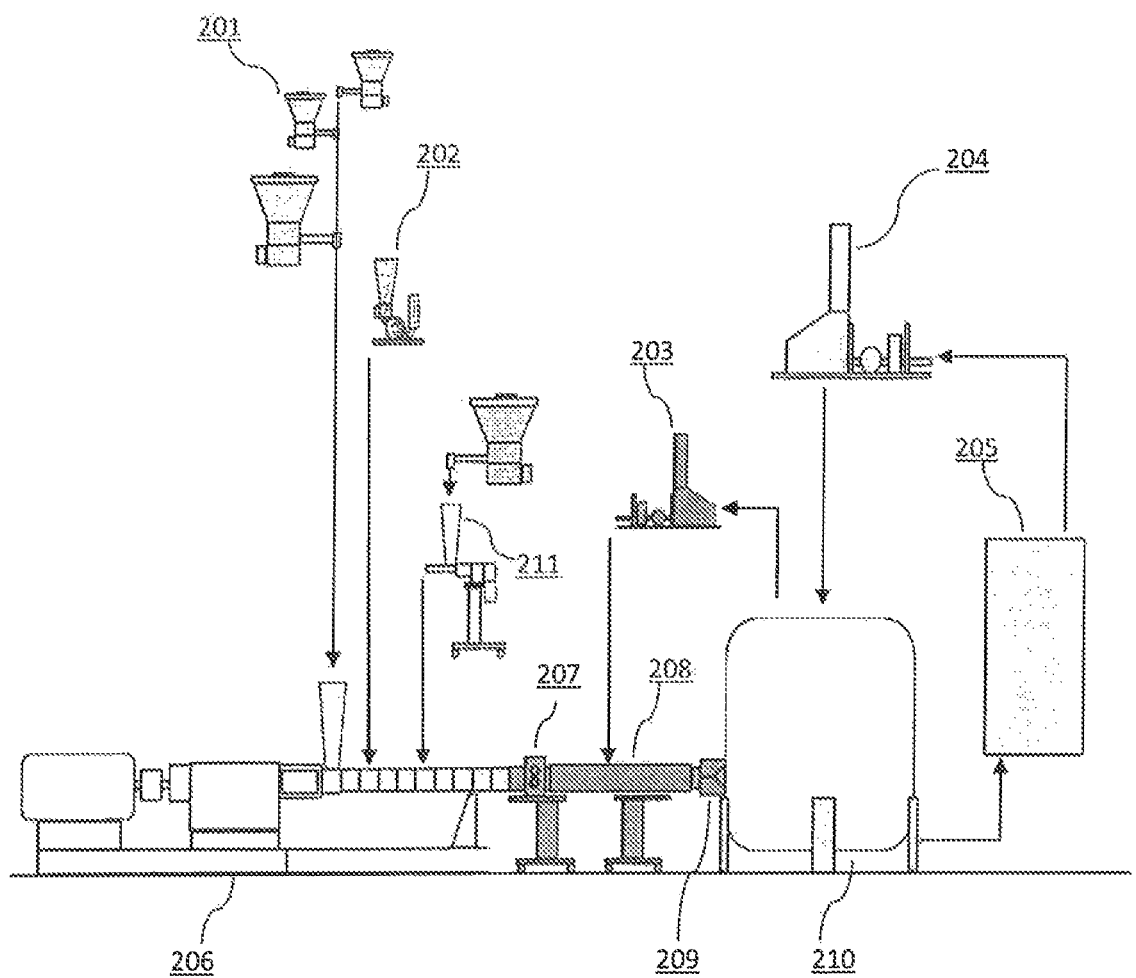
FIG. 2 illustrates the Continuous Cellulosic Processor System.

FIG. 2 illustrates the Continuous Cellulosic Processor System displaying Dry-Ingredient Feeders (201), Liquid Ingredient Feeder (202), $CO_2$ Injection System (203), Water Slurry Skid (204), Cellulose Dewatering Sieve (205), Twin Screw Extruder (206), Gear Pump (207), Mixer Cooler (208), Die (209), Collection Vessel (210).

Figure 3:
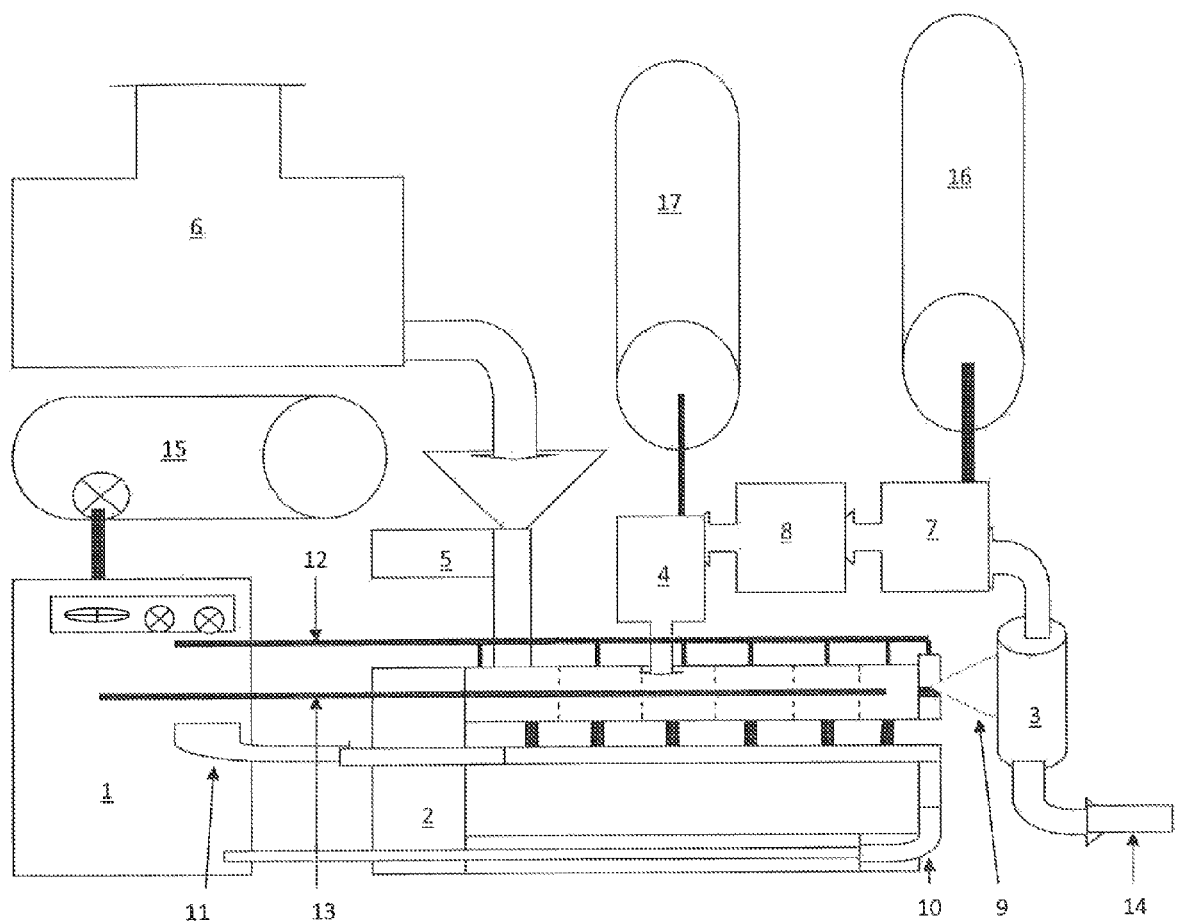
FIG. 3 illustrates the Continuous Supercritical Reactive Extrusion System.

FIG. 3 illustrates the Continuous Supercritical Reactive Extrusion System displaying Automated control system (1), Extruder (2), Expansion chamber (3), Pre-treatment Medium Feed (4), Cellulose Fiber Crammer-Feeder (5), Raw Material Size Reduction (6), $H_2O$ Condenser (7), Pre-Treatment Medium Compressor (8). Pressure Regulation Die (9), Temperature Control Medium Return (10), Temperature Control Medium Feed Lines (11), Chemical Feed lines (12), Control Lines From Pressure/Temperature Transducers (13), Pre-Treated Material Take-Off (14), Chemical Supply (15), Condensate Storage (16), Pre-Treatment Medium Supply (17).

Figure 4:
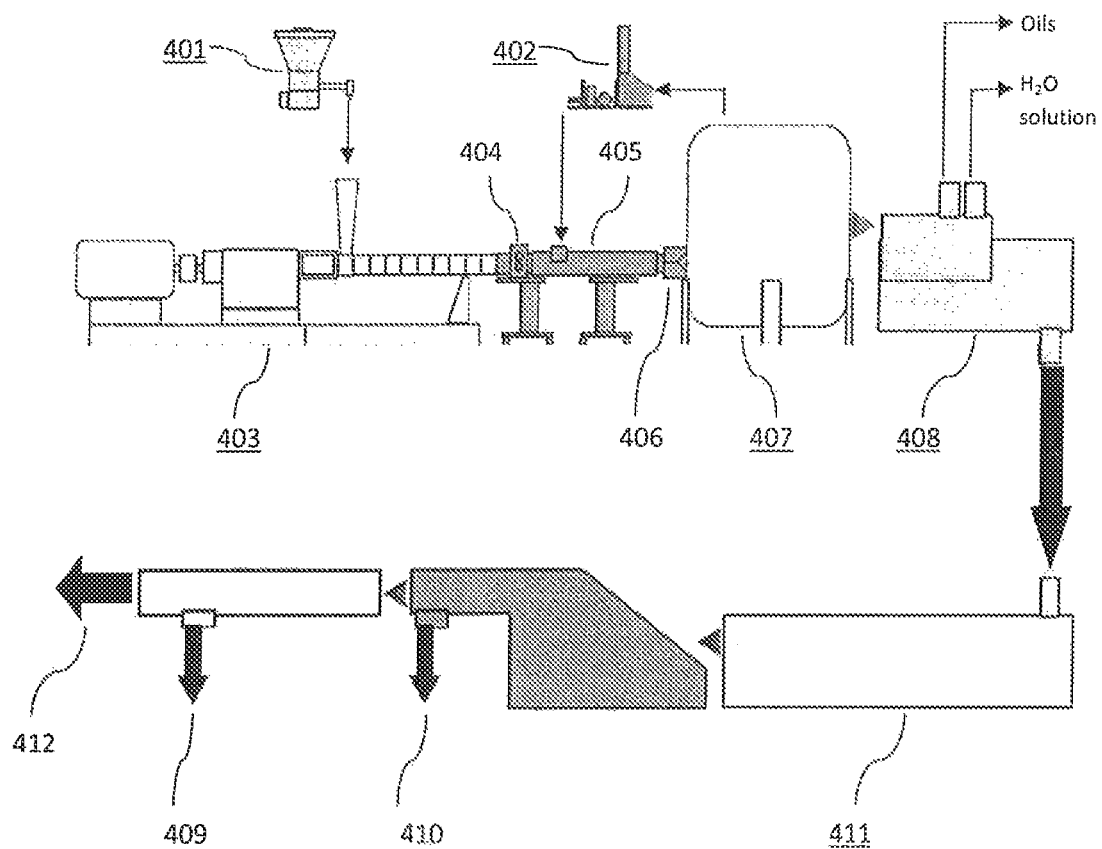
FIG. 4 illustrates the synergistic method of extracting oil and protein fractions of grains while pre-treating the fiber.

FIG. 4 illustrates the synergistic method of extracting oil and protein fractions of grains while pre-treating the fiber, displaying Dry Ingredient Feeder (401), $CO_2$ Injection System (402), Twin Screw Extruder (403), Gear Pump (404), Mixer Cooler (405), Die (406), Collection Vessel (407), Solid/Liquid Multistage Separator (408), Cellulose Fiber (409), Usable Protein Solids (410), Solid Cake Processing (411), Waste (412).

The Invention can be described by one or more of the following items.

Item 1. A method comprising of injecting a stream of medium capable of reacting with a lignocellulostic fiber component contained in a variety of natural plants, for processing in a continuous pretreatment process wherein the cellulose is surrounded by a protective sheath of hemicellulose and lignin.

Item 2. A process described according to item 1 wherein the method of processing is accomplished with an extruder configured for feeding of the material into the extruder screws and exiting on a continuous basis.

Item 3. A process described according to item 1 wherein the reactant is injected into the extruder at one or more locations along the extruder barrel.

Item 4. A process described according to item 1 wherein the reactant is one of a group of materials including, but not limited to Ammonia, Anhydrous Ammonia, Supercritical Carbon Dioxide.

Item 5. A process described according to item 1 wherein the extruder is a co-rotating twin screw extruder with intermeshing screw flights.

Item 6. A process described according to item 1 wherein the extruder is a co-rotating twin screw extruder with non-intermeshing screw flights.

Item 7. A process described according to item 1 wherein the extruder is a counter-rotating twin screw extruder with non-intermeshing screw flights.

Item 8. A process described according to item 1 wherein the extruder is a counter-rotating twin screw extruder with intermeshing screw flights.

Item 9. A process described according to item 1 wherein the extruder is a single screw extruder.

Item 10. A process described according to item 1 wherein the extruder rotation speed (rpm) is maintained in a range of between 10 and 1000 rpm's.

Item 11. A process described according to item 1 wherein the treatment is carried out by subjecting the feedstock to a temperature ranging from 10 degree. C. to 200 degree. C.

Item 12. A process described according to item 1 wherein the treatment is carried out by subjecting the feedstock to an average temperature ranging from 10 degrees C. to 100 degrees C.

Item 13. A process described according to item 1 wherein the treatment is carried out by subjecting the feedstock to an average temperature ranging from 20 degree. C. to 100.degree. C.

Item 14. A process described according to item 1 wherein the treatment is carried out by subjecting the feedstock to an average of pH 0.5 to 9.5.

Item 15. A process described according to item 1 wherein the treatment is carried out by subjecting the feedstock to an average of pH 4.5 to 7.5.

Item 16. A process described according to item 1 wherein the treatment is carried out by subjecting the feedstock to an average of pH 5.5 to 6.5.

Item 17. A process described according to item 1 wherein the treatment is carried out by subjecting the feedstock for a period of 5 seconds to 5 minutes.

Item 18. A process described according to item 1 wherein the treatment is carried out by subjecting the feedstock to a period of 10 seconds to 3 minutes.

Item 19. A process described according to item 1 wherein the treatment is carried out by subjecting the feedstock for a period of 30 seconds to 1 minute.

Item 20. A process described according to items 1 & 10 wherein the treatment is carried out by subjecting the feedstock to an extruder rotation speed (rpm) is maintained in a range of between 50 and 500 rpm's.

Item 21. A process described according to items 1 & 10 wherein the treatment is carried out by subjecting the feedstock to an extruder rotation speed (rpm) is maintained in a range of between 100 and 300 rpm's.

Item 22. A process described according to items 1 & 4 wherein the treatment is carried out by subjecting the feedstock to an extruder screw especially designed to effect a disruption of the cellulose cell wall without destroying the integrity of the cell structure.

Item 23. A process described according to items 1 & 4 wherein the treatment is carried out by subjecting the feedstock to an extruder especially designed to force-feed the feedstock into the extrusion system by way of a feeding system that keeps the feed throat tightly packed so as to prevent back-flow of gasses and liquids from the feed section of the extruder.

Item 24. A process described according to items 1 & 4 wherein the treatment is carried out in an extruder with a vapor lock consisting of a segment in the screw in which the flights are substantially reduced in height so as to cause a compaction of feedstock creating a dense blockage that resists "blowback" of vapors and liquids out of the feed port of the extruder.

Item 25. A process described according to items 1 & 4 wherein the treatment is carried out in an extruder equipped with feed ports to allow entry of liquids and/or gasses into the feedstock as it is being conveyed through the extruder.

Item 26. A process described according to items 1 & 4 wherein the treatment is carried out in an extruder equipped with four to twelve individual zones to allow regulation of the temperature separately in each zone.

Item 27. A process described according to items 1 & 4 wherein the treatment is carried out in an extruder equipped with a pressure regulating system to allow variable pressures at the exit port of the extruder.

Item 28. A process described according to items 1, 4 & 27 wherein the treatment is carried out at a pressure of between 500 to 3000 pounds per square inch (psi) at the exit point of the extruder.

Item 29. A process described according to items 1, 4 & 27 wherein the treatment is carried out at a pressure of 1000 to 2000 psi at the exit point of the extruder.

Item 30. A process described according to items 1, 4 & 27 wherein the treatment is carried out in an extruder equipped with a pressure regulating die to allow automatic decline of the pressure as the extrudate exits the extruder barrel.

Item 31. A process described according to items 1, 4 & 27 wherein the treatment is carried out in an extruder equipped with a pressure regulating die designed to allow automatic decline of the pressure to 1000 500 psi as the extrudate exits the extruder barrel.

Item 32. A process described according to items 1, 4 & 27 wherein the treatment is carried out in an extruder equipped with a pressure regulating die to allow automatic decline of the pressure, to less than 100 psi as the extrudate exits the extruder barrel.

Item 33. A process described according to Items 1, 4 & 27 wherein the treatment is carried out in an extruder equipped with a system designed to remove volatiles from the extrudate, preferably by vacuum to enhance the rapid devolatization and desired pressure drop.

Item 34. A process described according to items 1, 4 & 27 wherein the treatment is carried out in an extruder equipped with a decompression chamber designed to facilitate the rapid pressure drop and allow for anticipated expansion of the extrudate.

Item 35. A process described according to items 1, 4 & 34 wherein the treatment is carried out in an extruder equipped with a volatiles recycling system designed to recover and reuse volatiles such as ammonia or $CO_2$.

Item 36. A process described according to items 1, 4 & 34 wherein the treatment is carried out in combination with other types of cellulose pre-treatment including ultrasonic energy.

Item 37. A process described according to items 1, 4 & 27 wherein the treatment is carried out in an extruder equipped with a device such as a static mixer and a dosing system is attached to the outlet of the extruder, such device so designed to inject gas or liquid pretreatment medium into the feed stock and provide intensive dispersion of the medium determined amount of time.

Item 38. A process described according to items 1, 4 & 27 wherein the treatment is carried out utilizing a materials pump equipped with a device such as a static mixer and a dosing system is attached to the outlet of the extruder, such device so designed to inject gas or liquid pretreatment medium Into the feed stock and provide intensive dispersion of the medium for a determined amount of time.

Item 39. A process described according to items 1, 4, 27 & 37 wherein the treatment is carried out in an extruder equipped with a device such as a static mixer and a dosing system is attached to the outlet of the extruder, such device so designed to inject supercritical fluid pretreatment medium into the feed stock and provide intensive dispersion of the medium while retaining supercritical state for a determined amount of time.

Item 40. A process described according to items 1, 4, 27 & 37 wherein the treatment is carried out utilizing a materials pump equipped with a device such as a static mixer and a dosing system is attached to the outlet of the extruder, such device so designed to inject supercritical fluid pretreatment medium into the feed stock and provide intensive dispersion of the medium while retaining supercritical state for a determined amount of time.

Item 41. A continuous method of separating the oil content of bran by passing the product through a series of mechanical processes utilizing extrusion in combination with various chemicals and separation devices.

Item 42. A continuous method of separating the protein content of bran by passing the product through a series of mechanical processes utilizing extrusion in combination with various chemicals and separation devices.

Item 43. A continuous method of pre-treating the lingnicellulose content of bran by passing the product through a series of mechanical processes utilizing extrusion in combination with various chemicals and separation devices.

Item 44. A continuous method as described in items 1, 2 & 3 whereby the bran product is passed through an extruder in which the configuration and operating parameters are controlled to achieve a predetermined amount of pressure and cell disruption caused by the mechanical shear.

Item 45. A continuous method as described in items 1, 2, 3 & 4 whereby the extruder can be a single screw or twin screw type.

Item 46. A continuous method as described in items 1, 2, 3 & 4 whereby the pressure can range from 250 to 10,000 pounds per square inch.

Item 47. A continuous method as described in item 6 whereby the pressure vessel is any of a type that will facilitate the continuous movement of the extrudate through the system while maintaining the pressure required for the time frame allocated.

Item 48. A continuous method as described in items 6 & 7 whereby a pressurized mixer is an integral part of the extraction system and may or may not be directly attached to the extruder however, attached is preferred to more efficiently allow retaining the pressure on the extrudate as it is transferred into the pressurized mixer.

Item 49. A continuous method as described in items 6 & 7 whereby the pressure in the pressurized mixing vessel can or will be maintained by injection of pressurized fluids or gasses.

Item 50. A continuous method as described in items 6 & 7 whereby the pressure can be maintained in the range necessary to sustain supercritical status for a given period of time as desired.

Item 51. A continuous method as described in items 1, 2, 3, 4 & 9 whereby the feed stock for supercritical fluid applications can be, but not limited to; Ammonia, Carbon Dioxide, Methanol & Ethanol Alcohols.

Item 52. A continuous method as described in items 1, 2, 3, 4 & 9 whereby the preferred supercritical fluid is Supercritical Carbon Dioxide.

Item 53. A continuous method as described in items 6 & 7 whereby an outlet die is attached to the pressurized mixer to allow the rapid depressurizing of the extrudate, causing extensive disruption of the bran components.

Item 54. A continuous method as described in items 6, 7 & 13 whereby the outlet die is can be adjusted to maintain a desired pressure within the pressurized mixer thereby regulating outflow.

Item 55. A continuous method as described in items 1, 2, 3 & 4 whereby processing aids such as $H_2O$, Urea, plasticizers, etc., can be added to the bran at any chosen point in the extrusion/mixing process.

Item 56. A continuous method as described in items 1, 2, 3, 4 &, 13 whereby a collection device is attached to the pressurized mixer to facilitate the transfer of the processed bran into further devices such as a multi-stage centrifuge to separate the oil, $H_2O$, & solids.

Item 57. A continuous method as described in items 1, 2, 3, 4, 13 & 16 whereby a collection system is attached to the extrudate collector to capture any escaping gasses such as Carbon Dioxide and recycle the usable elements.

Item 58. A continuous method as described in item 16 whereby the solids component is further transferred to a solids separation system to separate the protein faction of the processed bran from the disrupted cellulosic portion of the processed bran.

Item 59. A continuous method as described in items 16 & 17 whereby the solids component Is further transferred to a second solids separation system to separate the pre-heated cellulosic faction from the waste portion of the processed bran.

The invention can also be described by one or more of the following paragraphs.

A novel continuous system for processing cellulose consisting of the following steps: pretreating said cellulose for the purpose of destructurizing the cellulosic fiber component, comprising of the following steps: preconditioning said feedstock by size reduction and regulating the moisture content, conveyance of the preconditioned feedstock through a range of options in processing equipment, the addition of processing aids and reactant chemicals.

The system wherein the reactant is one or more of a group of materials including, but not limited to Ammonia, Anhydrous Ammonia, Supercritical Carbon Dioxide, methanol, ethanol, Supercritical Water, etc.

The system wherein the reactant is injected into the system at selected locations in the system known to optimize the reaction effect.

The system whereby processing aids such as $H_2O$, Urea, plasticizers, etc, can be added to the preconditioned feedstock at any chosen point in the process system.

The system wherein the extruder is a co-rotating twin screw extruder with intermeshing screw flights, a co-rotating twin screw extruder with non-intermeshing screw flights, a counter-rotating twin screw extruder with non-intermeshing screw flights, a counter-rotating twin screw extruder with intermeshing screw flights, a single screw extruder or a materials pump; any of these examples of which is capable of forcing the preconditioned feedstock through the process system under the required process conditions.

The system wherein the system operating parameters can be synchronized between pressure, shear, speed and temperature to have the desired effect on the feedstock.

The system wherein the treatment action Is carried out by maintaining the feedstock in Supercritical Fluid state.

The system wherein the preferred reactant chemical is Carbon Dioxide.

The system wherein the feedstock treatment action is carried out by in a pH range of 3.5 to 9.5.

The system wherein the treatment action is carried out by adjusting the feedstock to a preferred pH range of 5.5 to 7.5.

The system wherein a condition of the biomass feedstock is size reduction to a range of 150 to 1000 microns.

The system wherein the treatment action is carried out by controlling the process temperature and pressure necessary to maintain the reactant chemical in Supercritical State for the finite period of time while feedstock continuously passes through the system.

The system wherein the treatment action is carried out by subjecting the feedstock in Supercritical Fluid condition for a period of 5 seconds to 5 minutes.

The system wherein the treatment is carried out by subjecting the feedstock in Supercritical Fluid condition for a period of 10 seconds to 3 minutes.

The system wherein the treatment is carried out by subjecting the feedstock in Supercritical Fluid condition for a period of 30 seconds to 1 minutes.

The system wherein the feedstock is conveyed into the system utilizing items such as rotary valves so as to prevent back-flow of gasses and liquids from downstream portion of the process.

The system wherein the treatment is carried out in a system equipped with feed ports to allow entry of liquids and/or gasses into the feedstock as it is being conveyed through the system.

The system wherein the treatment is carried out in a system equipped with a pressure regulating system to enable variable pressures at the exit port of the extruder.

The system wherein the treatment is carried out at a pressure of between 500 to 10,000 pounds per square inch (psi) at the exit point of the extruder.

The system wherein the treatment is carried out at a preferred pressure of 1,200 to 2,500 psi at the exit point of the extruder The system wherein the treatment is carried out in a system equipped with a pressure regulating die designed to automatically allow instant release of the destructurized extrudate as it exits the system while maintaining the desired process pressure within the system.

The system wherein the treatment is carried out in a system equipped to remove volatiles from the destructurized extrudate, preferably by vacuum to enhance the rapid devolatization and desired pressure drop.

The system wherein the treatment is carried out in a system equipped with a decompression chamber designed to facilitate the rapid pressure drop and allow for anticipated expansion of the destructurized extrudate.

The system wherein the treatment Is carried out in a system equipped with a volatiles recycling system designed to recover and reuse volatiles generated in the process such as ammonia, water or $CO_2$.

The system wherein the treatment is carried out in combination with other types of cellulose pre-treatment including ultrasonic energy.

The system wherein the treatment is carried out in a system equipped with a mixing device such as a static mixer to provide intensive dispersion of the feedstock for a determined amount of time.

The system wherein the treatment is carried out in a system equipped with an attachment to the mixing device, such attachment so designed to inject gas or liquid pretreatment medium into the feed stock, such medium being intensively dispersed into the feedstock as the feedstock is passing through the static mixer while under supercritical state.

The system wherein a preferred a condition of the biomass feedstock is size reduction to a range of 20 to 40 microns.

The system wherein a condition of the biomass feedstock is a desired moisture range of 10 to 90 percent.

The system wherein a condition of the biomass feedstock is a preferred moisture range of 40 to 60 percent.

The system wherein the pretreatment feedstock is grain bran.

The system whereby the pretreatment process of Destructurization of bran feedstock causes the partial release of the lipids and proteins entrapped in the destructurized bran product.

The system whereby the destructurization of bran feedstock pretreatment process of results in a 10 to 30 percent reduced extraction cost of lipids and protein components from the destructurized bran.

The system whereby the preferred extruder is a single screw design.

The system whereby the destructurized bran component is further transferred to a solids separation system to separate the protein faction of the processed bran from the Destructurized cellulosic portion of the processed bran.

The system whereby the destructurized bran component is further transferred to a solids separation system to separate the lipids faction of the processed bran from the Destructurized cellulosic portion of the processed bran.

The system whereby the outlet die is can be manually or automatically adjusted to maintain a desired pressure within the pressurized mixer thereby regulating outflow.

The system whereby a collection device is attached to the pressurized mixer to facilitate the transfer of the processed bran into further devices or extraction systems to separate the lipids, $H_2O$, & solids.

The system whereby a collection system, is attached to the extrudate collector to capture any escaping gasses such as Carbon Dioxide and recycle the usable elements.

The system whereby the solids component is further transferred to a second solids separation system to separate the pre-treated cellulosic faction from the waste portion of the processed bran.

The preceding described discoveries are intended to provide added efficiencies and lower the cost of the processes by which the non-starch portions of a starch to ethanol process are converted higher value added by-products.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present subject matter. For example, cellulose fiber Destructurization is also useful for biomass-based production facilities which produce alcohols other than ethanol. Such alcohols include, but are not limited to, food grade alcohol, industrial alcohols such as methanol, isopropanol, butanol, and so forth, further including propane diol, which can be used to make bioplastics. It is also likely that cellulose fiber Destructurization would be useful in biomass-based production facilities that produce various organic acids, such as Succinic or Malic acid. Most likely such production facilities which produce alcohols other than ethanol and/or organic acids consist of processes which utilize pretreatment technologies and processes described herein." Therefore, it is manifestly intended that embodiments of this invention be limited only by the claims and the equivalents thereof.

I claim:

1. A continuous process for destructurizing cellulose consisting of the following steps:
   pretreating said cellulose for the purpose of destructurizing cellulosic fiber component of the cellulose by continuously flowing the cellulose through an extruder into an attached static mixer while injecting a reactant converted into a supercritical condition with a supercritical fluid;
   aggressively mixing the cellulose in the static mixer while being held in the supercritical condition; and
   suddenly releasing the content from the static mixer with a simultaneous pressure drop causing a violent expansion of the supercritical fluid from within the cellulosic fiber component of the cellulose.

2. The continuous process according to claim 1 wherein the reactant is one or more materials selected from the group consisting of Ammonia, Anhydrous Ammonia, Supercritical Carbon Dioxide, methanol, ethanol, and Supercritical Water.

3. The continuous process according to claim 1 wherein the reactant is injected into the system at selected locations in the system known to optimize the reaction effect.

4. The continuous process according to claim 1, wherein processing aids selected from the group consisting of $H_2O$, Urea, and plasticizers are added at any chosen point in the process.

5. The continuous process according to claim 1 wherein the extruder is selected from the group consisting of a co-rotating twin screw extruder with intermeshing screw flights, a co-rotating twin screw extruder with non-intermeshing screw flights, a counter-rotating twin screw extruder with non-intermeshing screw flights, a counter-rotating twin screw extruder with intermeshing screw flights, a single screw extruder or a materials pump.

6. The continuous process according to claim 5 wherein the extruder and static mixer can be synchronized between pressure, shear, speed and temperature to have the desired effect on the cellulosic fiber component of the cellulose.

7. The continuous process according to claim 1 wherein the reactant is Carbon Dioxide.

8. The continuous process according to claim 1 wherein the process is carried out in a pH range of 3.5 to 9.5.

9. The continuous process according to claim 1 wherein the process is carried out by adjusting the feedstock to a pH range of 5.5 to 7.5.

\* \* \* \* \*